(12) United States Patent
Kim et al.

(10) Patent No.: US 7,820,414 B2
(45) Date of Patent: Oct. 26, 2010

(54) **XYLITOL DEHYDROGENASE-INACTIVATED AND ARABINOSE REDUCTASE-INHIBITED MUTANT OF *CANDIDA TROPICALIS*, METHOD OF PRODUCING HIGH-YIELD OF XYLITOL USING THE SAME, AND XYLITOL PRODUCED THEREBY**

(75) Inventors: Jung Hoe Kim, Daejeon (KR); Byoung Sam Ko, Gwangju (KR)

(73) Assignees: LPBIO Co., Ltd., Seoul (KR); Korea Advanced Institute of Science and Technology, Daejeon (KR)

( * ) Notice: Subject to any disclaimer, the term of this patent is extended or adjusted under 35 U.S.C. 154(b) by 369 days.

(21) Appl. No.: 11/771,081

(22) Filed: Jun. 29, 2007

(65) Prior Publication Data

US 2009/0004704 A1 Jan. 1, 2009

(51) Int. Cl.
*C12P 7/18* (2006.01)
*C12P 19/02* (2006.01)
*C12N 1/10* (2006.01)

(52) U.S. Cl. .................. 435/105; 435/158; 435/254.22

(58) Field of Classification Search ........................ None
See application file for complete search history.

(56) References Cited

U.S. PATENT DOCUMENTS 7,226,761 B2 * 6/2007 Miasnikov et al. .......... 435/105

OTHER PUBLICATIONS

Ko, Byoung Sam, et al., "Enhancement of xylitol productivity and yield using a xylitol dehydrogenase gene-disrupted mutant of *Candida tropicalis* under fully aerobic conditions," *Biotechnol Lett*, 2006, vol. 28, pp. 1159-1162.

Ko, Byoung Sam, et al., "Production of xylitol from D-xylose by a xylitol dehydrogenase gene-disrupted mutant of *Candida tropicalis*," *Applied and Environmental Microbiology*, Jun. 2006, pp. 4207-4213.

* cited by examiner

*Primary Examiner*—Herbert J. Lilling
(74) *Attorney, Agent, or Firm*—Rothwell, Figg, Ernst & Manbeck, P.C.

(57) ABSTRACT

Disclosed herein are Xylitol dehydrogenase-inactivated and arabinose reductase-inhibited mutant of *Candida tropicalis*, a method of producing a high yield of xylitol using the same, and xylitol produced by the method. More specifically, disclosed are a method for producing a high yield of xylitol, in which a high concentration of xylose contained in a biomass hydrolyzate is converted to xylitol using xylitol dehydrogenase-inactivated mutant of *Candida tropicalis*, without controlling dissolved oxygen to a low level, as well as xylitol produced according to the method. Also disclosed are a xylitol production method, in which the production of byproduct arabitol, which is produced when using a biomass as a substrate and adversely affects the yield of xylitol, is significantly reduced through the use of *Candida tropicalis* mutant ara-89 (KCTC 11136bp) having an inhibited activity of arabinose reductase converting arabinose to arabitol, thus increasing xylitol productivity, as well as xylitol produced by the method.

7 Claims, 3 Drawing Sheets

XYLITOL DEHYDROGENASE-INACTIVATED AND ARABINOSE REDUCTASE-INHIBITED MUTANT OF *CANDIDA TROPICALIS*, METHOD OF PRODUCING HIGH-YIELD OF XYLITOL USING THE SAME, AND XYLITOL PRODUCED THEREBY

BACKGROUND OF THE INVENTION

1. Field of the Invention

The present invention relates to Xylitol dehydrogenase-inactivated and arabinose reductase-inhibited mutant of *Candida tropicalis*, method of producing high-yield of xylitol using the same, and xylitol produced thereby. More specifically, the present invention relates to a xylitol production method, in which an inconvenience that concentration of dissolved oxygen in a xylitol-producing medium should be maintained at a very low level can be eliminated through the use of a xylitol dehydrogenase-inactivated mutant of *Candida tropicalis*, and the production of byproduct arabitol, which is produced when using a biomass as a substrate and adversely affects the yield of xylitol, can be significantly reduced through the use of *Candida tropicalis* mutant ara-89 (KCTC 11136bp), having an inhibited activity of arabinose reductase converting arabinose to arabitol, thus increasing the production of xylitol, as well as xylitol produced by the method.

2. Description of the Prior Art

Xylitol, a five-carbon sugar alcohol, has high sweetening power, and thus is widely used as a functional sugar substitute for sugar. Because xylitol is found naturally in a variety of fruits or vegetables in very small amounts, the extraction of xylitol from fruits or vegetables is not industrially advantageous. For this reason, xylitol is produced by a chemical method of reducing a hemicellulose hydrolyzate rich in xylose. However, in the chemical method, it is difficult to isolate and purify xylose or xylitol from other hydrolyzates occurring in the hemicellulose moiety, a lot of costs are incurred and the yield of xylitol is as low as about 50-60%. Also, it is a high-temperature and high-pressure employing alkali, which causes problems of risk and waste.

In recent attempts to overcome such shortcoming, biological methods for producing xylitol have been actively studied. Korean Patent Registration No. 1999819 discloses a method of producing xylitol, in which new strain *Candida tropicalis* is cultured in a medium, containing xylose, a nitrogen source and inorganic salts, to convert xylose to xylitol. Also, PCT International Patent Publication No. WO88/05467 discloses a method of producing xylitol from a high concentration of xylose by culturing *Candida guilliermondii* under conditions employing limited aeration. Such biological methods can employ, as a raw material, a relatively low purity of xylose compared to the chemical methods and are safe and environment-friendly, because the processes themselves are carried out at room temperature and atmospheric pressure. Thus, studies focused on the production of xylitol by a variety of bacteria, yeasts, fungi and recombinant yeasts have been conducted to produce xylitol in high productivity and high yield (Winkelhausen, E. et al., J. Ferment. Bioeng. 86:1-14, 1998; Granström, T. B. et al., Appl. Microbiol. Biotechnol. 74:277-281, 2007). However, bacteria and recombinant yeast strains were not suitable for the production of xylitol, because they showed a weak metabolic activity of producing xylose or low efficiency. However, among yeast strains, *Candida* sp strains are known as strains suitable for the biological production of xylitol, because they show high xylitol productivity and yield compared to other microorganisms.

According to studies conducted to date, it is known that, as shown in FIG. 1, *Candida* sp strains, such as *C. guillermondi*, *C. parapsilosis* and *C. tropicalis*, convert xylose, absorbed from cells, to xylitol by xylose reductase, and converts xylitol to xylulose by xylitol dehydrogenase. Xylulose is then converted to xylulose-5-phosphate by xylulokinase, and xylulose-5-phosphate is used for the growth and maintenance of cells through a pentose phosphate pathway (see Laplace, J. M. et al., Appl. Microbiol. Biotechnol., 36:158-162, 1991; Hahn-Hagerdal, B. et al., Enzyme Microb. Technol., 16:933-943, 1994). That is, xylitol-producing strains use xylose as a carbon source for cell growth. Xylitol converted from xylose by xylose reductase is then converted to xylulose by xylitol dehydrogenase, and in this case, when the aeration of the medium is limited such that the concentration of dissolved oxygen is maintained as low as 0.5-2.0%, intracellular redox imbalance is incurred to reduce the supply of nicotinamide adenine dinucleotide (NAD) as a cofactor required by xylitol dehydrogenase and inhibit the conversion of xylitol to xylulose. As a result, xylitol is accumulated in cells and media, and thus xylitol is produced from xylose in a yield of 60-80%. That is, in the prior technology of producing xylitol using xylitol-producing strains, it is necessary to limit aeration to maintain the concentration of dissolved oxygen at a low level. Thus, studies focused on enhancing the productivity and yield of xylitol by limiting the aeration of medium to maintain the concentration of dissolved oxygen at a low level so as to intentionally induce intracellular redox imbalance have been actively conducted (see Kim, S. Y. et. al., J. Ferment. Bioeng., 83(3):267-270, 1997; Korean Patent Publication No. 1996-030577).

Japanese Patent No. 1998276791 discloses a method of producing xylitol using a concentrated *Candida parapsilosis* strain at a dissolved oxygen concentration of 0.1-5.0%. However, when xylitol is produced using an industrial scale fermenter, it is substantially impossible to control the concentration of dissolved oxygen to a low level as described above, and even if the control is possible, the production yield is only about 70-80%. Also, there is processing inconvenience, as Korean Patent Registration No. 10-0259470 suggests an agitation rate for controlling oxygen transfer rate for optimizing xylitol production to microaerobic conditions corresponding to a DOT (percent concentration of oxygen in medium) of less than 1%.

Paying attention to the fact that xylitol produced in *Candida* sp strains is reduced by its conversion to xylulose by xylitol dehydrogenase, the present inventors have developed xylitol dehydrogenase-inactivated *Candida tropicalis* mutant, in which xylitol produced from xylose can no longer be used for cell growth, and thus xylose can be bioconverted to xylitol with a theoretical yield of 100% (Ko, B. S. et. al., Appl. Environ. Microbiol. 72:4207-4213, 2006). Thus, the present inventors filed an application for the protection of an invention relating to a method of producing xylitol in high yield using a xylitol-producing strain, in which the expression of xylitol dehydrogenase is inhibited (Korean Patent Application No. 10-2005-0079751, filed on Aug. 30, 2005).

Also, according to said invention, xylitol yield should reach a theoretical yield of 100%, but when a biomass hydrolyzate containing a large amount of xylose is used directly as a substrate, byproduct arabitol that adversely affects xylitol crystallization as the final step of the production process will be produced in large amounts, and xylitol productivity and final xylitol concentration will be so low that industrial economy cannot be achieved. For this reason, there is a need to develop to a novel technology that enhances productivity and minimizes the production of byproducts.

SUMMARY OF THE INVENTION

Accordingly, the present invention has been made in order to solve the above-mentioned problems occurring in the prior art, and it is a first object of the present invention to provide a method for producing a high yield of xylitol, which can eliminate the inconvenience that the aeration of medium in a process of producing xylitol using a xylitol-producing strain should be limited to maintain the concentration of dissolved oxygen at a low level.

It is a second object of the present invention to provide a method for producing a high yield of xylitol, which can minimize the production of byproduct arabitol, which is produced in a process of producing xylitol using a biomass hydrolyzate.

It is a third object of the present invention to provide a method for producing a high yield of xylitol, which can solve the shortcoming in that when a biomass hydrolyzate is used directly as a substrate, xylitol productivity and final xylitol concentration will be low.

To achieve the above objects, in one aspect, the present invention provides a method of producing a high yield of xylitol using a xylitol dehydrogenase-inactivated mutant of *Candida tropicalis*, the method comprising inoculating and culturing the *Candida tropicalis* mutant in medium, wherein the culture is carried out under fully aerobic conditions without a separate process of controlling the concentration of dissolved oxygen in the medium to a low level of 0.5-2%.

In the above xylitol production method, the substrate component is a biomass hydrolyzate.

The xylitol production method is preferably performed through fed-batch culture using, as a feeding solution, a mixture of the biomass hydrolyzate and a carbon source.

The biomass hydrolyzate is preferably a corncob hydrolyzate, a sugarcane bagasse hydrolyzate, a coconut byproduct or a hydrolyzate of *Betula platyphylla* var. *japonica*.

The carbon source is preferably glycerol.

Also, in the xylitol production method, the concentration of dissolved oxygen in the culture medium is higher than 5%.

In another aspect, the present invention provides a xylitol dehydrogenase-inactivated and arabinose reductase-inhibited mutant of *Candida tropicalis*, and a method of producing a high yield of xylitol using the same. More specifically, the present invention provided *Candida tropicalis* mutant ara-89 (KCTC 11136bp) having a inhibited activity of arabinose reductase converting arabinose to arabitol, selected from xylitol dehydrogenase-inactivated mutant of *Candida tropicalis* by treatment with methanesulfonic acid ethylester (EMS) through random mutagenesis, as well as a method of producing a high yield of xylitol using said *Candida tropicalis* mutant ara-89 (KCTC 11136bp).

In the xylitol production method, the culture of the mutant is preferably carried out under fully aerobic conditions without a separate process of controlling the concentration of dissolved oxygen to a low level of 0.5-2%, and a biomass hydrolyzate is preferably used as a substrate.

The xylitol production method is preferably performed through fed-batch culture using, as a feeding solution, a mixture of the biomass hydrolyzate and a carbon source.

The biomass hydrolyzate is preferably a corncob hydrolyzate, a sugarcane bagasse hydrolyzate, a coconut byproduct or a hydrolyzate of *Betula platyphylla* var. *japonica*.

The carbon source is preferably glycerol.

Also, in the xylitol production method, the concentration of dissolved oxygen in the culture is higher than 5%.

In yet another aspect, the present invention provides xylitol produced by any one of the above xylitol production methods.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION OF THE INVENTION

Hereinafter, the inventive method for producing a high yield of xylitol using a xylitol dehydrogenase-inactivated mutant of *Candida tropicalis* will be described in detail with reference to the accompanying drawings.

Figure 1:
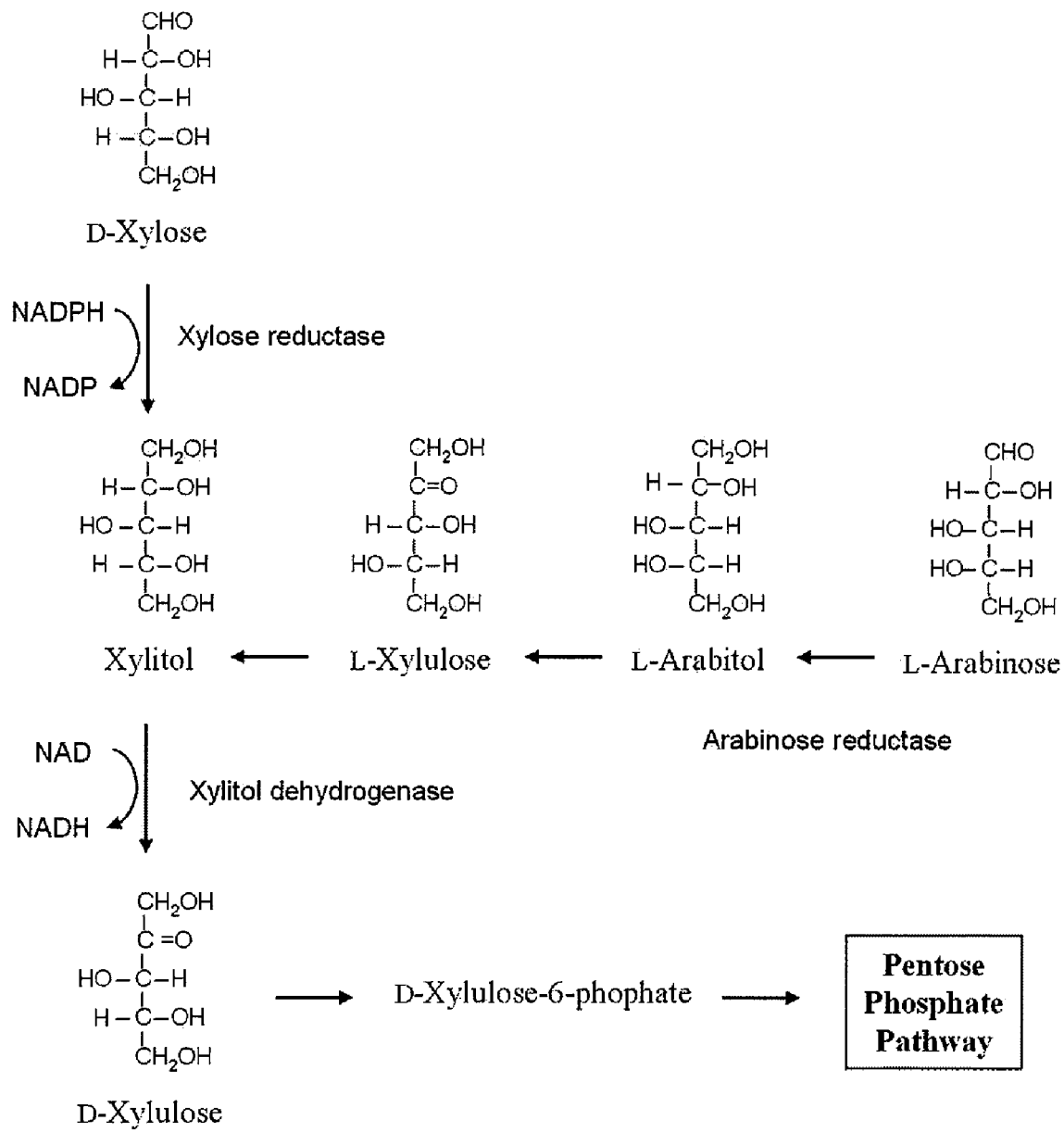
FIG. 1 shows xylose and arabinose metabolic pathways by a xylitol-producing strain.

FIG. 1 shows xylose and arabinose metabolic pathways by a xylitol-producing strain.

Figure 2:
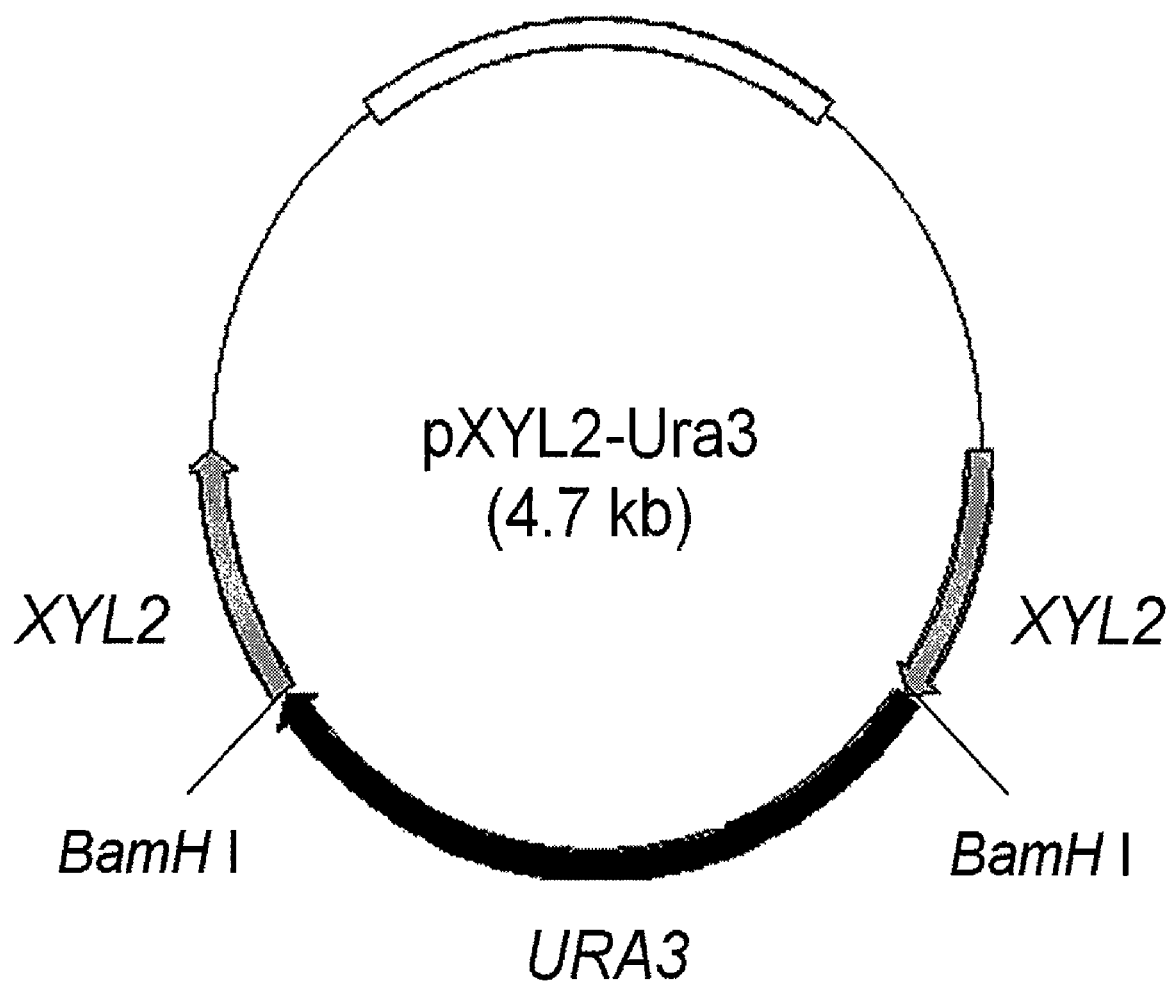
FIG. 2 is a genetic map of a pXYL2-Ura3 transformation vector for constructing a xylitol dehydrogenase-inactivated mutant of *Candida tropicalis*, according to a preferred embodiment of the present invention.

FIG. 2 is a genetic map of a pXYL2-Ura3 vector for constructing a xylitol dehydrogenase-inactivated mutant of *Candida tropicalis*, according to a preferred embodiment of the present invention.

A process of constructing a *Candida tropicalis* mutant lacking the activity of xylitol dehydrogenase and producing xylitol using the constructed mutant is as follows.

When a pXYL2-Ura3 transformation vector is introduced into *Candida tropicalis*, a xylitol dehydrogenase gene is selectively removed through an intracellular mechanism of homologous recombination, and thus a transformed strain, which cannot grow in a medium containing only xylose as a carbon source, can be constructed.

In the xylitol dehydrogenase-inactivated mutant of *Candida tropicalis*, because xylitol converted from xylose is no longer used for cell growth, xylose cannot be used as a carbon source, and thus cell growth does not occur. Only when a carbon source such as glycerol or glucose other than xylose is added to medium, cells can grow using the carbon source. Thus, xylose is used only as a substrate for xylitol production, and the carbon source is used to grow cells and supply nicotinamide adenine dinucleotide phosphate-reduced form (NADPH) as a cofactor required by xylose reductase. In particular, in the case of the xylitol dehydrogenase-inactivated mutant, because there is no need to induce redox imbalance for the enhancement of xylitol yield and production, unlike the existing strain, it was anticipated that the concentration of dissolved oxygen in a culture process would not need to be controlled to a low level. Also, because yeast strains can use glycerol as a carbon source under aerobic conditions, it was anticipated that, when glycerol is used as a co-substrate, cell growth rate and NADPH supply rate can be influenced by aeration rate.

Thus, the xylitol dehydrogenase-inactivated mutant of *Candida tropicalis* was inoculated into a xylitol-producing medium containing xylose, glycerol, yeast extract, $KH_2PO_4$ and $MgSO_4 \cdot 7H_2O$, and experiments for producing xylitol in various aeration conditions were carried out. The aeration rate was controlled by the agitation speed of an agitator. The experimental results showed that xylitol production rate was high when the agitation speed was higher than a given level, that is, when aeration rate was high. This suggests that the assimilation of glycerol in cells is affected by aeration rate, and an increase in aeration rate leads to an increase in the assimilation of glycerol and an increase in the supply rate of NADPH, resulting in an increase in xylitol productivity. Also, the yield of xylitol from xylose was constant in a range of 97-98% regardless of aeration rate, suggesting that xylitol was produced in a theoretical yield of almost 100%, because xylitol dehydrogenase activity was eliminated regardless of intracellular redox imbalance.

Biomasses, such as corncobs, sugar cane stems, coconut byproducts and *Betula platyphylla* var. *japonica*, are rich in hemicelluloses including xylose, arabinose and glucose, and particularly, have a high content of xylose. Thus, hydrolyzates of the biomasses can be used directly for the production of xylitol. In the present invention, xylitol was produced using, as a substrate, a corncob hydrolyzate consisting of 83.5% xylose, 5.3% glucose and 11.2% arabinose, and using glycerol as a co-substrate. The xylitol-producing strain consumed all of glucose contained in the hydrolyzate for cell growth and showed a xylitol yield of 97.2% and a xylitol productivity of 3.24 g/L/h.

Moreover, a high concentration of xylitol was produced using fed-batch culture while the concentration of xylose in the medium was maintained at less than 100 g/L, because a high xylose concentration of more than 100 g/L would be unfavorable for cell growth and xylitol production. During the production of xylitol, a mixture of a corncob hydrolyzate as a xylose raw material with glycerol as a carbon source for cell growth and NADPH supply was continuously supplied. As a result, xylitol was produced in a yield of 97% and a productivity of 2.67 g/L/h. Glucose contained in the corncob hydrolyzate was completely consumed during the cell culture process. Also, 15.2 g/L corresponding to 57% of the total concentration (26.5 g/L) of arabinose added remained as arabinose, and 11.3 g/L corresponding to 43% was converted to arabitol.

Hereinafter, the inventive method of producing a high yield of xylitol using arabinose reductase-inhibited mutant of *Candida tropicalis* ara-89 (KCTC 11136bp) will be described in detail with reference to the accompanying drawings.

Figure 3:
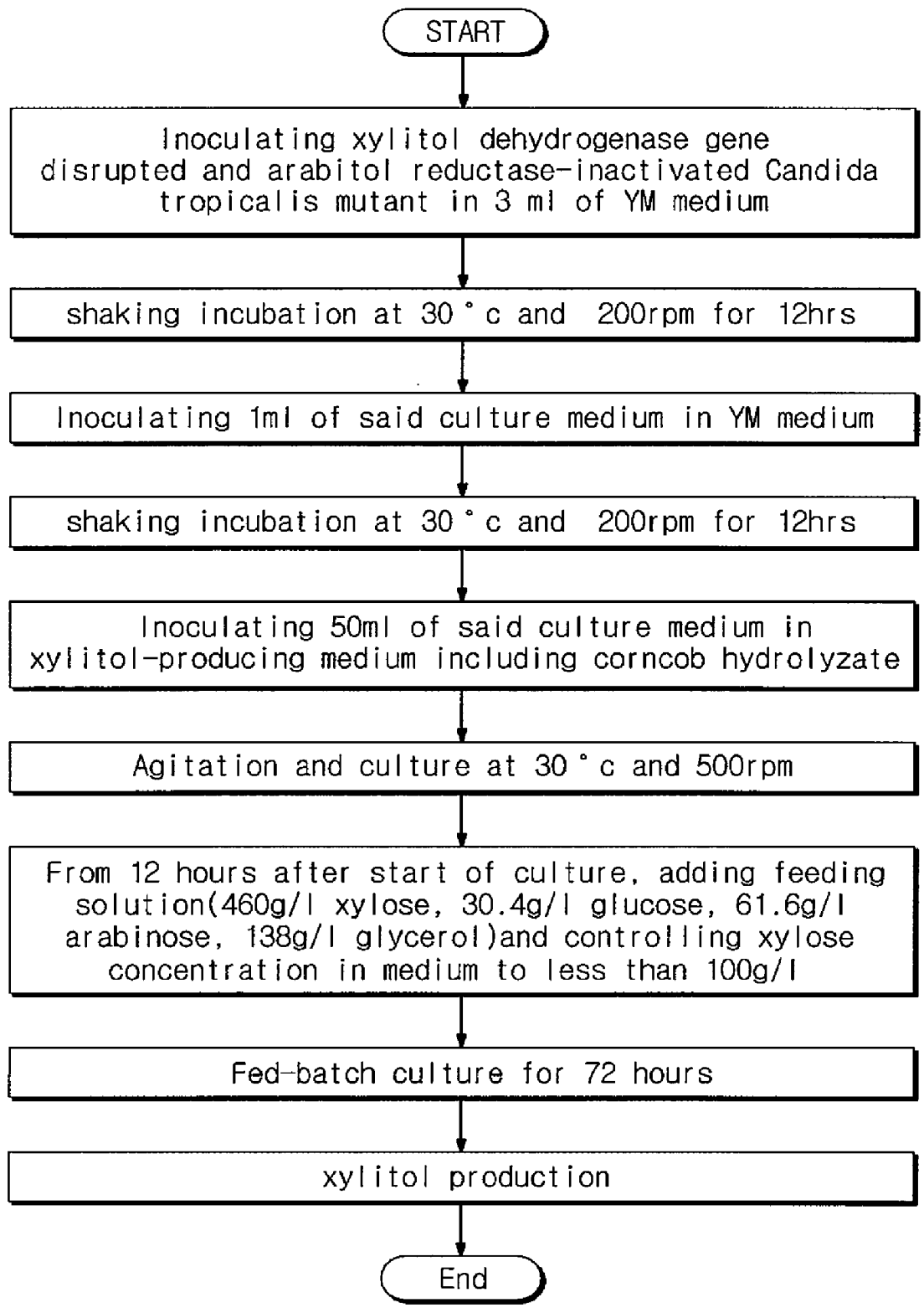
FIG. 3 is a flow chart showing a method of producing xylitol using a *Candida tropicalis* mutant (KCTC 11136bp) according to a preferred embodiment of the present invention.

FIG. 3 is a flow chart showing a method of producing xylitol using xylitol dehydrogenase-inactivated and arabinose reductase-inhibited mutant of *Candida tropicalis* (KCTC 11136bp), according to a preferred embodiment of the present invention.

The mutant ara-89 (KCTC 11136bp) having an inhibited activity of arabinose reductase converting arabinose to arabitol was selected from xylitol dehydrogenase-inactivated mutants of *Candida tropicalis* using, as an alkylating agent, methanesulfonic acid ehtylester (EMS) inducing random mutagenesis. That is, the present inventors have developed a mutant strain in which a cellular metabolic process of converting arabinose to arabitol was inhibited by mutation to reduce arabitol productivity. The enzymatic activities of the mutant strain were measured and, as a result, the activity of xylose reductase converting xylose to xylitol was the same as that of the parent strain, whereas the activity of arabonose reductase converting arabinose to arabitol was decreased by 63%.

Also, xylitol production was carried out through fed-batch culture using the mutant strain and, as a result, xylitol was produced in a yield of 97% with a productivity of 2.80 g/L/h. Glucose contained in the corncob hydrolyzate was completely consumed during the culture process. In addition, 23.7 g/L corresponding to 85% of the total amount (27.9 g/l) of arabinose added, remained as arabinose, and 4.2 g/L corresponding to 15% was converted to arabitol.

Hereinafter, the present invention will be described in further detail with reference to examples.

Example 1

To clone unknown *Candida tropicalis* xylitol dehydrogenase gene, the gene homology between already known *Pichia stipitis* xylitol dehydrogenase and genes belonging to the medium-chain alcohol dehydrogenase family, including sorbitol dehydrogenase, alcohol dehydrogenase and threonine dehydrogenase, was investigated. Using the resulting highly conserved region as a template, PCR was performed using the following primers (SEQ ID NO: 1 and SEQ IN NO: 2) in the following conditions to obtain a 1,095-bp *Candida tropicalis* xylitol dehydrogenase gene: 1 min at 94 □, 25 cycles of 30 sec at 94 □, 30 sec at 58 □and 30 sec at 72 □, and 3 min at 72 □. The amplified *Candida tropicalis* xylitol dehydrogenase gene was cloned into a pGEM-T easy vector (BIONEX, Korea), a BamHI site was introduced into the middle of the xylitol dehydrogenase gene, and an ura3 gene was introduced into the introduced BamHI site, thus obtaining a 4.7-kb pXYL2-Ura3 transformation vector as shown in FIG. 2.

primer F: 5'-aatggtcttgggtcacgaatcc-3' (SEQ ID NO: 1); and primer R: 5'-gctctgaccaagtcgtaggcttc-3' (SEQ ID NO: 2).

The obtained vector pXYL2-Ura3 was introduced into *Candida tropicalis*, which was then plated on an Urasil-deficient solid screening medium (6.7 g/L yeast nitrogen base (amino acid-free), 20 g/L glucose, and 15 g/L agar powder) and incubated at 30 □for 2 days.

Then, each of the colonies formed on the solid medium was inoculated onto a xylose-containing solid medium (6.7 g/L yeast nitrogen base (amino acid free), 20 g/L xylose, and 15 g/L agar powder) and a glucose-containing solid medium (6.7 g/L yeast nitrogen base (amino acid free), 20 g/L glucose, and 15 g/L agar powder). Then, they were incubated at 30 □for 2 days. Then, a strain, which did not grow on the xylose-containing solid medium and grew only on the glucose-containing solid medium, was selected, thus obtaining xylitol dehydrogenase-inactivated mutant of *Candida tropicalis*.

The present inventors performed the following examples using the mutant strain newly selected for use in the present invention, instead of using a mutant strain selected at the time of a previous application (Korean Patent Application No. 10-2005-0079751) relating to said *Candida tropicalis* mutant strain, and did not deposit the newly selected mutant strain in an international depository authority for microorganisms. In the present invention, the newly selected mutant strain was named "BS-xdh1" for convenience of description.

Example 2

The effects of medium aeration and oxygen transfer rate on xylitol yield and productivity in the production of xylitol using the xylitol dehydrogenase-inactivated mutant of *Candida tropicalis* BS-xdh1 were investigated.

The xylitol dehydrogenase-inactivated mutant of *Candida tropicalis* BS-xdh1 was inoculated in 3 ml of YM medium (20 g/L glucose, 3 g/L yeast extract, 3 g/L malt extract, and 5 g/L bacto-peptone) and cultured in a shaking incubator at 30 □and 200 rpm for 12 hours. Then, 1 ml of the culture medium was inoculated in 50 ml of YM medium and cultured in a shaking incubator at 30 □and 200 rpm for 12 hours.

Then, 50 ml of the culture medium was inoculated in a fermenter containing 1 liter of a xylitol-producing medium (50 g/L xylose, 20 g/L glycerol, 10 g/L yeast extract, 5 g/L $KH_2PO_4$ and 0.2 g/L $MgSO_4 \cdot 7H_2O$, pH 4.5) and cultured at for 24 hours with agitation at 300, 400 and 500 rpm, and the changes in dry cell weight, xylose, glycerol and xylitol concentrations with the passage of time were measured. Specifically, the dry cell weight was calculated by measuring the absorbance of the sample at 600 nm with a spectrophotometer (Shimadzu, Japan) and converting the measured value using a predetermined standard curve. Also, the sample was centrifuged and the supernatant was analyzed with an HPLC (Shimazu, Japan) system (Sugar-Pak I column (Waters, USA); refractive index detector (Waters, USA); solvent: water; flow rate: 0.5 ml/min; column temperature: 90 □) to measure the concentrations of xylose, glycerol and xylitol. The measurement results are shown in Table 1 below.

TABLE 1

Effects of aeration on xylitol yield and productivity in the production of xylitol using the xylitol dehydrogenase-inactivated mutant of *Candida tropicalis* BS-xdh1

| | Agitation speed (rpm) | | |
|---|---|---|---|
| Time (h) | 300 Xylitol concentration (g/l) | 400 Xylitol concentration (g/l) | 500 Xylitol concentration (g/l) |
| 0 | 0.0 | 0.0 | 0.0 |
| 6 | 1.6 | 1.9 | 1.1 |
| 12 | 8.4 | 13.9 | 38.3 |
| 15 | 13.6 | 35.4 | 48.4 |
| 18 | 18.1 | 49.0 | 48.4 |
| 24 | 30.4 | 47.5 | 48.2 |

As shown in Table 1, in the case of an agitation speed of 500 rpm corresponding to the highest oxygen transfer rate, 48.4 g/L of xylitol was produced in a culture time of 15 hours, whereas agitation speeds of 400 rpm and 300 rpm showed xylitol productions of 35.4 g/L and 13.6 g/L, respectively, suggesting that xylitol productivity was proportional to agitation speed. Although not shown in Table above, the production of xylitol was no longer increased at an agitation speed higher than 500 rpm.

Such results suggest that the assimilation rate of glycerol in cells is affected by aeration rate, and until dissolved oxygen is sufficient, an increase in oxygen transfer rate leads to an increase in the assimilation rate of glycerol and an increase in NADPH supply rate, resulting in an increase in xylitol production rate. Also, the production yield of xylitol from xylose was constant in a range of 97-98% independent of aeration rate, suggesting that xylitol was produced in a theoretical yield of almost 100%, because xylitol dehydrogenase activity was eliminated regardless of intracellular redox imbalance.

Thus, when the xylitol-producing strain was used to produce xylitol, xylitol could be produced even in high productivity and a theoretical yield of almost 100% in an industrial large-scale fermenter, because there was no need to maintain the dissolved oxygen level as low as 0.5-2.0%. Also, when the yeast strain is cultured in a low-dissolved-oxygen condition, byproducts such as ethanol and glycerol, which reduce xylitol yield and inhibit xylitol purification and crystallization, will be produced, whereas, in the case of the xylitol dehydrogenase gene-disrupted mutant strain, a more efficient process could be constructed, because a high level of dissolved oxygen could be maintained so that byproducts such as ethanol and glycerol were not produced.

Example 3

Xylitol was produced using a corncob hydrolyzate as a substrate.

The xylitol dehydrogenase-inactivated mutant of *Candida tropicalis* BS-xdh1 was cultured in the same conditions as in Example 2, and 50 ml of the culture medium was inoculated in a fermenter containing 1.0 liter of a xylitol-producing medium (100 g/L xylose, 6.6 g/L glucose, 13.4 g/L arabinose, 30 g/L glycerol, 10 g/L yeast extract, 5 g/L $KH_2PO_4$ and 0.2 g/L $MgSO_4 \cdot 7H_2O$, pH 4.5) including a corncob hydrolyzate (83.5% xylose, 5.3% glucose and 11.2% arabinose) and was cultured at 30 □ for 30 hours with agitation at 500 rpm. Then, the changes in dry cell weight and xylose, glucose, arabinose, arabitol, glycerol and xylitol concentrations with the passage of time were measured. The measurement of dry cell weight and xylose, glucose, arabinose, arabitol, glycerol and xylitol concentrations was carried out in the same manner as described in Example 2. The measurement results are shown in Table 2 below.

TABLE 2

Results of production of xylitol in high yield and high productivity through batch culture using corncob hydrolyzate

| Time (h) | Dry cell weight (g/L) | Xylose concentration (g/L) | Glycerol concentration (g/L) | Arabinose concentration (g/L) | Arabitol concentration (g/L) | Xylitol concentration (g/L) |
|---|---|---|---|---|---|---|
| 0 | 0.2 | 100.0 | 30.0 | 13.4 | 0.0 | 0.0 |
| 6 | 1.5 | 100.0 | 29.8 | 13.4 | 0.0 | 0.0 |
| 12 | 12.2 | 96.7 | 28.3 | 12.2 | 1.0 | 3.2 |
| 18 | 16.3 | 62.2 | 18.7 | 10.8 | 2.1 | 35.7 |
| 24 | 15.0 | 20.9 | 9.0 | 9.6 | 3.1 | 78.5 |
| 30 | 15.2 | 0.0 | 2.3 | 9.2 | 3.8 | 97.2 |

As can be seen from the results in Table 2, the xylitol-producing mutant consumed all of glucose for cell growth and used glycerol as a co-substrate. Also, xylitol was produced in an amount of 97.2 g/L for 30 hours using, as a substrate, xylose contained in the corncob hydrolyzate in a large amount, and some of arabinose was converted to arabitol. Herein, xylitol yield was 97.2%, and xylitol productivity was 3.24 g/L/h.

In this Example, the xylitol yield was the same as the case of using pure xylose, and the xylitol productivity was similar thereto. Thus, when an inexpensive biomass hydrolyzate rather than pure xylose is used as a substrate for xylitol production, it will be advantageous for increasing the economy of production technology and will be environment-friendly, because biomass waste is recycled.

Example 4

A high concentration of xylitol was produced using fed-batch culture while the xylose concentration in medium was maintained at less than 100 g/L, because a high xylose concentration of more than 100 g/L would interfere with cell growth and xylitol production.

The xylitol dehydrogenase-inactivated mutant of *Candida tropicalis* BS-xdh1 was cultured in the same conditions as in Example 1, and 50 ml of the culture medium was inoculated in a fermenter containing 1 liter of a xylitol-producing medium (50 g/L xylose, 3.3 g/L glucose, 6.7 g/L arabinose, 20 g/L glycerol, 10 g/L yeast extract, 5 g/L $KH_2PO_4$ and 0.2 g/L $MgSO_4.7H_2O$, pH 4.5) prepared using a corncob hydrolyzate and was cultured with shaking at 30 □ and 500 rpm. From 12 hours after the start of the culture, a feeding solution (460 g/L xylose, 30.4 g/L glucose, 61.6 g/L arabinose and 138 g/L glycerol) containing a corncob hydrolyzate was added, and the resulting culture medium was subjected to fed-batch culture for 72 hours while the xylose concentration in the medium was controlled to less than 100 g/L. The changes in dry cell weight and xylose, glucose, arabinose, arabitol, glycerol and xylitol concentrations with the passage of time were measured in the same manner as described in Example 2. The measurement results are shown in Table 3 below.

xylitol production yield. When biomass hydrolyzates as inexpensive xylose sources are used for the production of xylose, a given amount of arabitol will be produced, and when the amount thereof is higher than a given concentration, it will reduce xylitol production yield. For this reason, it is required to inhibit arabitol production.

Example 5

On the basis of the results of Example 4, a novel xylitol-producing strain, in which a cellular metabolic process of converting arabinose to arabitol was inhibited, was developed from the xylitol dehydrogenase-inactivated mutant of *Candida tropicalis* BS-xdh1 using methanesulfonic acid ethylester (EMS) as an alkylating agent.

For this purpose, the xylitol dehydrogenase-inactivated mutant of *Candida tropicalis* BS-xdh1 was inoculated in 3 ml of YM medium (20 g/L glucose, 3 g/L yeast extract, 3 g/L malt extract and 5 g/L of bacto-peptone 5 g/L) and was cultured at 30 □ for 24 hours with shaking at 200 rpm. Then, 30 ml of the culture medium was transferred into a 50-ml conical tube, and then the cells were washed two times with 30 ml of minimal A buffer (10.5 g/L $K_2HPO_4$, 4.5 g/L $KH_2PO_4$, 1.0 g/L $(NH_4)_2SO_4$ and 0.5 g/L sodium citrate). The cells were resuspended in 15 ml of minimal A buffer, and 450 □ of methanesulfonic acid ethylester (EMS) was then added thereto.

Then, the cells were incubated with shaking at 30 □ and 200 rpm for 90 minutes. Then, the cells were washed two

TABLE 3

Results of production of xylitol in high yield and high productivity through fed-batch culture using corncob hydrolyzate

| Time (h) | Dry cell weight (g/L) | Xylose concentration (g/L) | Glycerol concentration (g/L) | Arabinose concentration (g/L) | Arabitol concentration (g/L) | Xylitol concentration (g/L) |
|---|---|---|---|---|---|---|
| 0 | 0.6 | 50.0 | 20.0 | 6.7 | 0.0 | 0.0 |
| 12 | 17.5 | 24.5 | 7.5 | 5.3 | 1.0 | 24.5 |
| 24 | 26.1 | 29.8 | 13.1 | 11.8 | 5.3 | 92.5 |
| 36 | 30.8 | 29.0 | 9.9 | 14.4 | 7.5 | 134.2 |
| 48 | 28.4 | 13.2 | 4.0 | 11.8 | 9.1 | 160.3 |
| 60 | 30.4 | 17.5 | 1.7 | 13.6 | 9.9 | 175.0 |
| 72 | 30.8 | 21.9 | 6.7 | 15.2 | 11.3 | 192.3 |

As can be seen from the results in Table 3, when the production of xylitol was performed through fed-batch culture using a corncob hydrolyzate, xylitol was produced in a concentration of 192.3 g/L for 72 hours, indicating a xylitol yield of 97% and a xilytol productivity of 2.67 g/L/h. Glucose contained in the corncob hydrolyzate was completely consumed during the cell culture process, and 15.2 g/L corresponding to 57% of the total amount (26.5 g/l) of arabinose added remained as arabinose, and 11.3 g/L corresponding to 43% was converted to arabitol. Herein, the concentration of arabitol was 11.3 g/L, and the concentration of final xylitol concentration to arabitol concentration was 100:5.9.

Because the xylose reductase of yeast strains also has arabinose reductase activity, arabinose contained in biomass hydrolyzates can be inevitably converted to arabitol. Arabitol, a five-carbon sugar alcohol like xylitol, is a byproduct, which has a molecular structure and physical properties, similar to those of xylitol, and thus interferes with purification and crystallization processes in xylitol production so as to reduce times with 5 ml of minimal A buffer, resuspended in 2 ml of minimal A buffer and then dispensed on YM agar plate. Then, the cells were cultured at 30 □ for 2 days, and the resulting single colonies were inoculated and cultured in an arabitol-producing medium (20 g/L arabinose, 20 g/L glycerol and 10 g/L yeast extract) for 24 hours.

The concentrations of arabitol produced by the mutant strains were quantified using the HPLC analysis method described in Example 2, and mutant strains showing an arabitol production, which was 50% lower than that of the original strain, were selected. Each of these mutant strains was inoculated in 5 ml of a xylitol-producing medium (20 g/L xylose, 20 g/L glycerol and 10 g/L yeast extract) and cultured for 24 hours, and mutants strains showing a xylitol concentration, which was higher than 90% of that of the parent strain, were finally selected. The selection results are shown in Table 4 below.

TABLE 4

Selection of mutants showing inhibited arabitol production

| Mutant strains | Dry cell weight (g/L) | Arabitol concentration (g/L) | Xylitol concentration (g/L) |
|---|---|---|---|
| Parent strain | 5.5 | 3.9 | 19.7 |
| ara-06 | 4.9 | 1.9 | 16.6 |
| ara-26 | 5.1 | 1.8 | 17.9 |
| ara-51 | 3.9 | 1.3 | 15.4 |
| ara-77 | 5.1 | 1.7 | 18.1 |
| ara-89 | 5.3 | 1.7 | 19.6 |

As can be seen in Table 4, in the case of mutant strain 'ara-89', cell growth and xylitol concentration were almost similar to those of the parent strain as a control group, but arabitol concentration was decreased by 65% compared to the parent strain. To measure the enzymatic activity of mutant strain ara-89, the cells were inoculated and cultured in 50 ml of arabitol-producing medium (20 g/L arabinose, 20 g/L glycerol and 10 g/L yeast extract) for 12 hours, and then resuspended in 50 mM potassium phosphate buffer. Then, the suspension was sonicated five times for 20 seconds for each time to disrupt the cells. Then, the suspension was centrifuged and the supernatant was transferred into a 1.5-ml tube. The activity of each of xylose reductase and arabinose reductase was measured using a crude enzyme, 0.2 mM NADPH as a cofactor, and xylose or arabinose as a substrate. Herein, the enzymatic activity was analyzed by measuring the change in absorbance at 340 nm with a spectrophotometer (Shimadzu, Japan). The analysis results are shown in Table 5 below.

TABLE 5

Analysis of xylose and arabinose reductase activities of mutant showing inhibited arabitol production

| Mutant strain | Xylose reductase activity (mU) | Arabinose reductase activity (mU) |
|---|---|---|
| Parent strain | 324.9 | 354.7 |
| ara-89 | 317.5 | 131.2 |

As can be seen in the results in Table 5, in the case of mutant strain ara-89, the activity of xylose reductase converting xylose to xylitol was equal to that of the parent strain, whereas the activity of arabinose converting arabinose to arabitol was decreased by 63%.

The finally selected *C. tropicalis* mutant ara-89 having an inhibited activity of arabinose reductase was deposited in KCTC (Korean Collection for Type Cultures), an international depository authority for microorganisms, on Jun. 12, 2007 (Accession No. KCTC 11136bp).

Example 6

The mutant ara-89 (KCTC 11136bp) showing inhibited arabitol production was inoculated into 3 ml of YM medium (20 g/L glucose, 3 g/L yeast extract, 3 g/L malt extract and bacto-5 g/L peptone) and cultured in a shaking incubator at 30 □and 200 rpm for 12 hours. Then, 1 ml of the culture medium was inoculated again into 50 ml of YM medium and cultured in a shaking incubator at 30 □and 200 rpm for 12 hours.

Then, 50 ml of the culture medium was inoculated in a fermenter containing 1 liter of a xylitol-producing medium (50 g/L xylose, 3.3 g/L glucose, 6.7 g/L arabinose, 20 g/L glycerol, 10 g/L yeast extract, 5 g/L $KH_2PO_4$ and 0.2 g/L $MgSO_4.7H_2O$ 0.2 g/L, pH 4.5) including a corncob hydrolyzate and was cultured with agitation at 30 □and 500 rpm. From 12 hours after the start of the culture, a feeding solution (460 g/L xylose, 30.4 g/L glucose, 61.6 g/L arabinose and 138 g/L glycerol) containing a hydrolyzate was added to the medium, and the resulting culture medium was subjected to fed-batch culture for 72 hours while the xylose concentration in the medium was controlled to less than 100 g/L. The changes in dry cell weight and xylose, glucose, arabinose, arabitol, glycerol and xylitol concentrations with the passage of time were measured in the same manner as described in Example 2. The measurement results are shown in Table 6 below.

TABLE 6

Results of production of xylitol through fed-batch culture using *C. tropicalis* mutant ara-89 (KCTC 11136 bp) showing inhibited arabitol production

| Time (h) | Dry cell weight (g/L) | Xylose concentration (g/L) | Glycerol concentration (g/L) | Arabinose concentration (g/L) | Arabitol concentration (g/L) | Xylitol concentration (g/L) |
|---|---|---|---|---|---|---|
| 0 | 0.7 | 50.0 | 20.0 | 6.7 | 0.0 | 0.0 |
| 12 | 16.3 | 26.1 | 9.2 | 5.5 | 0.2 | 22.7 |
| 24 | 25.1 | 28.1 | 12.5 | 12.8 | 1.3 | 90.9 |
| 36 | 28.7 | 26.0 | 10.4 | 16.4 | 1.9 | 137.6 |
| 48 | 28.9 | 12.2 | 8.5 | 18.4 | 2.4 | 169.5 |
| 60 | 29.1 | 13.5 | 7.6 | 20.2 | 3.0 | 175.0 |
| 72 | 29.0 | 5.8 | 3.3 | 23.7 | 4.2 | 201.3 |

As can be seen from the results in Table 6, when the production of xylitol was performed through fed-batch culture using the new mutant strain, xylitol was produced for 72 hours was produced in a concentration of 201.3 g/L for 72 hours, suggesting a xylitol yield of 97% and a xylitol productivity of 2.80 g/L/h. Glucose contained in the corncob hydrolyzate was completely consumed during the cell culture process, and 23.7 g/L corresponding to 85% of the total amount (27.9 g/l) of arabinose added remained as arabinose, and 4.2 g/L corresponding to 15% was converted to arabitol. Herein, the concentration of final xylitol concentration (201.3 g/L) to arabitol concentration (4.2 g/L) was 100:2.1, resulting from a decrease arabitol production of 65% compared to the parent strain.

Also, xylitol productivity was increased by 5% compared to the parent strain, suggesting that NADPH required for arabitol production was additionally used for xylitol production in an amount corresponding to the amount of inhibited arabitol production. As described above, using the newly developed xylitol-producing mutant having an inhibited activity of arabinose reductase, it was possible to complete an efficient process of producing xylitol in high yield and high productivity, in which the production of byproduct arabitol interfering with xylitol purification and crystallization was significantly inhibited.

Example 7

The mutant ara-89 (KCTC 11136bp) showing inhibited arabitol production was inoculated into 3 ml of YM medium (20 g/L glucose, 3 g/L yeast extract, 3 g/L malt extract and 5 g/L bacto-peptone) and culture in a shaking incubator at 30 □ and 200 rpm for 12 hours. Then, 1 ml of the culture medium was inoculated into 50 ml of YM medium and cultured in a shaking incubator at 30 □ and 200 rpm for 12 hours.

Then, 50 ml of the culture medium was inoculated in a fermenter containing 1 liter of a xylitol-producing medium (50 g/L xylose, 5.2 g/L glucose, 3.8 g/L arabinose, 20 g/L glycerol, 10 g/L yeast extract, 5 g/L KH$_2$PO$_4$ and 0.2 g/L MgSO$_4$.7H$_2$O, pH 4.5) including a sugarcane bagasse hydrolyzate and was cultured with agitation at 30 □ and 500 rpm. The level of dissolved oxygen in the culture process was preferably maintained at more than 5%. From 9 hours after the start of the culture, a feeding solution (460 g/L xylose, 30.4 g/L glucose, 61.6 g/L arabinose and 138 g/L glycerol) prepared using hydrolyzates was added to the medium, and the resulting culture medium was subjected to fed-batch culture for 72 hours while the xylose concentration in the medium was controlled to less than 100 g/L. The changes in dry cell weight and xylose, glucose, arabinose, arabitol, glycerol and xylitol concentrations with the passage of time were measured in the same manner as described in Example 2. The measurement results are shown in Table 7 below.

Also, the sugarcane bagasse hydrolyzate had an arabinose content lower than the corncob hydrolyzate by 43%, leading to a decrease in arabitol production of 50%. In addition, it had a high glucose content compared to the corncob hydrolyzate, leading to a decrease in carbon source glycerol, thus reducing production cost.

As described above, according to the present invention, xylitol dehydrogenase-inactivated and arabinose reductase-inhibited mutant of *Candida tropicalis* is used in xylitol production, and thus an efficient xylitol production process with high yield and high productivity can be achieved by inhibiting xylitol-to-xylulose conversion, inhibiting the production of byproduct arabitol, using a biomass hydrolyzate and also using fed-batch culture. Also, according to the present invention, because there is no need to control dissolved oxygen concentration to a low level through limited aeration, which was essential in the prior xylitol production method using microorganisms, an economic, safe and environment-friendly xylitol production process can be provided.

As described above, according to the inventive method of producing xylitol using the *Candida tropicalis* mutant BS-xdh1 lacking xylitol dehydrogenase activity, the use of the *Candida tropicalis* mutant BS-xdh1 eliminates a need to maintain a very low concentration of dissolved oxygen in medium.

Also, according to the present invention, the production of byproduct arabitol from arabinose contained in biomass hydrolyzates can be inhibited through the use of the *Candida tropicalis* mutant ara-89 (KCTC 11136bp) having an inhibited activity of arabinose reductase, thus enhancing xylitol productivity.

Furthermore, according to the inventive xylitol dehydrogenase-inactivated and arabinose reductase-inhibited mutant of *Candida tropicalis*, and the inventive method of a high yield of xylitol using the same, the production cost of xylitol can be reduced through the use of inexpensive biomass hydrolyzates containing a high concentration of xylose.

TABLE 7

Results of production of xylitol through fed-batch culture using *C. tropicalis* mutant ara-89 (KCTC 11136 bp), showing inhibited arabitol production, and sugar cane bagasse hydrolyzate

| Time (h) | Dry cell weight (g/L) | Xylose concentration (g/L) | Glycerol concentration (g/L) | Arabinose concentration (g/L) | Arabitol concentration (g/L) | Xylitol concentration (g/L) |
|---|---|---|---|---|---|---|
| 0 | 0.9 | 50.0 | 20.0 | 3.8 | 0.0 | 0.0 |
| 12 | 21.0 | 52.3 | 18.8 | 4.1 | 0.0 | 15.4 |
| 24 | 28.9 | 57.3 | 16.7 | 6.7 | 0.7 | 84.5 |
| 36 | 31.4 | 38.0 | 13.1 | 8.8 | 1.2 | 128.9 |
| 48 | 32.1 | 17.6 | 10.5 | 11.1 | 1.7 | 168.8 |
| 60 | 32.0 | 9.5 | 7.2 | 12.8 | 1.9 | 181.4 |
| 72 | 31.8 | 3.4 | 5.5 | 13.9 | 2.1 | 203.2 |

As can be seen from the results in Table 7, when the production of xylitol was performed through fed-batch culture using the new mutant strain, xylitol was produced for 72 hours was produced in a concentration of 203.2 g/L of 72 hours, suggesting a xylitol yield of 97% and a xylitol productivity of 2.82 g/L/h. Glucose, the component of the sugarcane bagasse hydrolyzate, was completely consumed during the cell culture process, and 13.9 g/L corresponding to 87% of the total amount (16.0 g/l) of arabinose added remained as arabinose, and 2.1 g/L corresponding to 11% was converted to arabitol. The concentration of final xylitol concentration (203.2 g/L) to arabitol concentration (2.1 g/L) was 100:1.0.

In addition, xylitol productivity and final xylitol concentration can be enhanced through the use of biomass hydrolyzates and the fed-batch culture process in which a xylose substrate and a carbon source for cell growth are distinguished from each other.

Although the preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A arabinose reductase-inhibited mutant of *Candida tropicalis* ara-89 (KCTC 11136bp), selected from xylitol dehydrogenase-inactivated mutant of *Candida tropicalis* BS-xdh1 by treatment with methanesulfonic acid ethylester (EMS) through random mutagenesis.

2. A method of producing a high yield of xylitol using the *Candida tropicalis* mutant ara-89 (KCTC 11136bp) of claim 1.

3. The method of claim 2, which comprises culturing the mutant under fully aerobic conditions without a separate process of controlling dissolved oxygen concentration to a low level of 0.5-2%, in which the culture is carried out using a biomass hydrolyzate as a substrate.

4. The method of claim 3, wherein the culture is performed through fed-batch culture using, as a feeding solution, a mixture of the biomass hydrolyzate and a carbon source.

5. The method of claim 3, wherein the biomass hydrolyzate is a corncob hydrolyzate, a sugarcane bagasse hydrolyzate, a coconut byproduct or a hydrolyzate of *Betula platyphylla* var. *japonica*.

6. The method of claim 4, wherein the carbon source is glycerol.

7. The method of claim 3, wherein the concentration of dissolved oxygen in the culture is higher than 5%.

* * * * *

SEQUENCE LISTING

<160> NUMBER OF SEQ ID NOS: 2

<210> SEQ ID NO 1
<211> LENGTH: 22
<212> TYPE: DNA
<213> ORGANISM: Artificial sequence
<220> FEATURE:
<223> OTHER INFORMATION: oligonucleotide primer with homology to Candida tropicalis

<400> SEQUENCE: 1
aatggtcttg ggtcacgaat cc                                              22

<210> SEQ ID NO 2
<211> LENGTH: 23
<212> TYPE: DNA
<213> ORGANISM: Artificial sequence
<220> FEATURE:
<223> OTHER INFORMATION: oligonucleotide primer with homology to Candida tropicalis

<400> SEQUENCE: 2
gctctgacca agtcgtaggc ttc                                             23